: ::

United States Patent
Ben Nun

(10) Patent No.: US 11,065,106 B2
(45) Date of Patent: Jul. 20, 2021

(54) TISSUE HOLDING APPARATUS

(71) Applicant: E.K.—D.D.S. LTD., Tel Aviv (IL)

(72) Inventor: Joshua Ben Nun, Bet Herut (IL)

(73) Assignee: E.K.—D.D.S. LTD, Tel Aviv (IL)

( * ) Notice: Subject to any disclaimer, the term of this patent is extended or adjusted under 35 U.S.C. 154(b) by 347 days.

(21) Appl. No.: 16/501,078

(22) Filed: Feb. 19, 2019

(65) Prior Publication Data

US 2019/0223997 A1    Jul. 25, 2019

Related U.S. Application Data

(63) Continuation of application No. 15/111,996, filed as application No. PCT/IL2015/050049 on Jan. 14, 2015, now Pat. No. 10,251,747.

(51) Int. Cl.
| | | |
|---|---|---|
| *A61F 2/14* | (2006.01) | |
| *A61F 9/007* | (2006.01) | |
| *A61F 9/008* | (2006.01) | |
| *A61B 18/12* | (2006.01) | |
| *A61B 18/14* | (2006.01) | |

(52) U.S. Cl.
CPC ............. *A61F 2/148* (2013.01); *A61B 18/12* (2013.01); *A61F 2/142* (2013.01); *A61F 9/007* (2013.01); *A61F 9/0081* (2013.01); *A61B 2018/1407* (2013.01); *A61F 2009/00872* (2013.01)

(58) Field of Classification Search
CPC ........ A61F 2/148; A61F 2/142; A61F 9/0081; A61F 9/007; A61F 2009/00872; A61B 18/12; A61B 2018/1407
See application file for complete search history.

(56) References Cited

U.S. PATENT DOCUMENTS

| | | | | |
|---|---|---|---|---|
| 5,098,439 | A | * 3/1992 | Hill | ............ A61F 2/1664 606/107 |
| 8,470,029 | B2 | * 6/2013 | Walter | ............ A61F 9/007 623/6.12 |
| 2006/0173539 | A1 | 8/2006 | Shiuey | |
| 2007/0208422 | A1 | 9/2007 | Walter et al. | |
| 2007/0282131 | A1 | 12/2007 | Huang et al. | |

(Continued)

FOREIGN PATENT DOCUMENTS

| | | |
|---|---|---|
| CN | 101495063 | 7/2009 |
| EP | 1472986 A1 | 11/2004 |

(Continued)

OTHER PUBLICATIONS

European Patent Office, Extended European Search Report for PCT/IL2015/050049, dated Sep. 26, 2017.

(Continued)

*Primary Examiner* — Amy R Weisberg
(74) *Attorney, Agent, or Firm* — Robert G. Lev

(57) ABSTRACT

A tissue holding assembly for endothelial implantation comprising an open frame having legs for engaging a stem, such that said frame is insertable between a stroma and a Descemet's membrane, said frame being coated with a biological adhesive for adhering to a perimeter of a section of the Descemet's membrane to adhere the section of the Descemet's membrane to the frame for surgical separation of said section by cutting therearound, wherein said frame further comprises a heating element around its inner perimeter.

7 Claims, 12 Drawing Sheets

(56) References Cited

U.S. PATENT DOCUMENTS

| | | |
|---|---|---|
| 2008/0281341 A1 | 11/2008 | Miller et al. |
| 2010/0211051 A1 | 8/2010 | Weston et al. |
| 2012/0059488 A1 | 3/2012 | Shimmura |
| 2012/0245592 A1 | 9/2012 | Berner et al. |
| 2013/0085567 A1 | 4/2013 | Tan et al. |
| 2013/0123916 A1 | 5/2013 | Nigam et al. |
| 2013/0253529 A1 | 9/2013 | Walter et al. |

FOREIGN PATENT DOCUMENTS

| | | |
|---|---|---|
| EP | 1981437 | 10/2008 |
| EP | 2601996 A1 | 6/2013 |
| JP | 2009524486 | 7/2009 |
| JP | 5312951 | 10/2013 |
| WO | WO 1994/21205 A1 | 9/1994 |
| WO | WO 2000/76403 A1 | 12/2000 |
| WO | WO 2007089508 | 8/2007 |
| WO | WO 2007132332 | 11/2007 |
| WO | WO 2007143111 | 12/2007 |
| WO | WO 2012/149468 A2 | 11/2012 |
| WO | WO 2014049591 | 4/2014 |
| WO | WO 2015/111040 A1 | 7/2015 |

OTHER PUBLICATIONS

William J. Reinhart et al., Deep Anterior Lamellar Keratoplasty as an Alternative to Penetrating Keratoplasty. Ophthalmology vol. 118, No. 1, pp. 209-218, Jan. 2011, doi: 10.1016/j.ophtha.2010.11.002.
John Thomas, Corneal Endothlial Transplant (DSAEK, DMEK & DLEK), Section 4 Surgical Instruments,pp. 108-119, table 11-1. Jaypee Brothers Medical Publishers Ltd, 2010 . . . URL: http://www.google.co.il/books?hl=en&lr=&id=LrJH35GlxO0C&oi=fnd&pg=PA1&dq=corneal+edothelial+thomas+John&ots=JHLLgKQtyK&sig=VuPeQGEtE8nYd6GHhpCS23DpTuw&redir_esc=y#v=onepage&q=corneal%20endothelial%20thomas%20John&f=false.
Patent Cooperation Treaty, International Search report for PCTIL2018051241.
Patent Cooperation Treaty, Written Opinion for PCT1L2018051241.

* cited by examiner

TISSUE HOLDING APPARATUS

PRIORITY INFORMATION

The subject application claims priority as a continuing application based on U.S. application Ser. No. 15/111,996, filed on Jul. 15, 2016, which claims priority from PCT Application No: PCT/IL2015/050049, filed on Jan. 14, 2015, and Israeli Patent Application No: 230567, filed on Jan. 21, 2014.

BACKGROUND

Corneal transplant surgery is required for the surgical treatment of endothelial diseases of the cornea including glaucoma, edema and Fuchs endothelial dystrophy.

The cornea is the transparent front part of the eye that covers the iris, pupil, and anterior chamber. The cornea, with the anterior chamber and lens, refracts light and accounts for approximately two-thirds of the eye's total optical power.

In humans, the refractive power of the cornea is approximately 43 diopters. While the cornea contributes most of the eye's focusing power, its focus is fixed. The curvature of the lens, on the other hand is adjusted by the eye muscles to "tune" the focal length of the eye, to bring objects at different distances into focus.

Because transparency is of prime importance, the cornea does not have blood vessels and no direct blood supply. It receives oxygen that first dissolves in the tears and then diffuses throughout the cornea to keep it healthy. It receives nutrients via diffusion from the tear fluid through the outside surface, from the aqueous humour through the inside surface, and also from neurotrophins supplied by nerve fibres that innervate it. In humans, the cornea has a diameter of about 11.5 mm and a thickness of 0.5-0.6 mm in the center, which drops off to about 0.6-0.8 mm at the periphery.

In humans (and other higher vertebrates) the cornea is fused with the skin to form a single multiple layers structure.

The human cornea, like those of other primates, has five layers. From the anterior to posterior the five layers of the human cornea are:
  (i) Corneal epithelium—this is an exceedingly thin multicellular epithelial tissue layer (non-keratinized stratified squamous epithelium) of fast-growing and easily regenerated cells that is kept moist with tears. Irregularity or edema of the corneal epithelium disrupts the smoothness of the air-tear film interface which is the most significant component of the total refractive power of the eye, thereby reducing visual acuity. The Corneal epithelium is continuous with the conjunctival epithelium, and consists of about 6 layers of cells which are shed constantly on the exposed layer and are regenerated by multiplication in the basal layer.
  (ii) Bowman's layer (also erroneously known as the anterior limiting membrane). This is a tough layer that protects the corneal stroma. It consists of similar irregularly arranged collagen fibers that are mainly type I collagen fibrils. These fibrils interact with and attach on to each other. The bowman's layer is 8 µm-14 µm thick.
  (iii) Corneal stroma (also known as the substantia propria). This is a thick, transparent middle layer consisting of regularly arranged collagen fibers along with sparsely distributed interconnected keratocytes, which are the cells for general repair and maintenance.—The keratocytes are parallel and are superimposed, in a manner analogous to book pages. The corneal stroma consists of approximately 200 layers of mainly type I collagen fibrils. Each layer is 1.5 µm-2.5 µm. The stroma is responsible for up to 90% of the corneal thickness.
  (iv) Descemet's membrane (also known as the posterior limiting membrane) is a thin cellular layer that serves as the modified basement membrane of the corneal endothelium, from which the cells are derived. This layer is composed mainly of collagen type IV fibrils which are less rigid than collagen type I fibrils, and are around 5 µm-20 µm thick, depending on the subject's age.
  (v) Corneal endothelium: a simple squamous or low cuboidal monolayer, approx 5 µm thick, of mitochondria-rich cells. These cells are responsible for regulating fluid and solute transport between the aqueous and corneal stromal compartments. The corneal endothelium is bathed with aqueous humor. Unlike the corneal epithelium the cells of the endothelium do not regenerate. Instead, they stretch to compensate for dead cells which reduce the overall cell density of the endothelium and have an impact on fluid regulation. If the endothelium can no longer maintain a proper fluid balance, stromal swelling due to excess fluids and subsequent loss of transparency will occur and this may cause corneal edema and interference with the transparency of the cornea and thus impairing the image formed.

The cornea is a protective domed layer of clear tissue covering the front of the eye. The endothelial cells are non-replicating. In normal healthy membranes there is a cell density of between about 1500 and 2500 cells per $mm^2$.

Once the population of endothelial cells decreased below a critical number that is about 600 per $mm^2$, the cornea becomes edematous while losing its optical quality. This condition is known as corneal edema.

In corneal edema, the cornea becomes overly hydrated by accumulated fluid. Corneal edema may result in deteriorated vision. If corneal edema becomes severe, blisters on the cornea can appear. In rare cases, surgery may be needed to treat corneal edema. In one technique, the cornea is replaced with a transplanted cornea.

Corneal edema is a result of a lack of viable cells in the corneal endothelium. The purpose of a surgical transplant is to replace a section of the corneal endothelium lacking healthy cells, with a section of donor endothelium having healthy cells. The complete replacement of the damaged cornea has been the treatment for corneal edema for many years. However, this approach has some disadvantages, including a high degree of post-operative astigmatism, a lack of predictable refractive outcome, and disturbance to the ocular surface.

Recently, the surgical trend has shifted towards removal of only a thin layer of tissue from a diseased eye and replacing it with corresponding donor tissue from a fresh human cadaver eye. The implanted tissue consists of the posterior corneal stroma, a thin layer of connective tissue known as Descemet's membrane that carries on its surface a monolayer of the endothelial cells. These cells actively "pump" the fluids from the cornea and maintain its clarity One surgical technique for replacing the Descemet's membrane is known as DSEK, which is an acronym for Descemet Stripping Endothelial Keratoplasty. DSEK is performed through a relatively small corneal incision compared to that required for standard perforating keratoplasty, thereby avoiding 'open sky' surgery with its risk of hemorrhage or expulsion, decreasing the incidence of postoperative wound dehiscence, and reducing unpredictable refractive outcomes. DSEK has dramatically changed the treatment of corneal endothelial disease.

It is believed that DSEK and similar techniques also decrease the rate of transplant rejection. However, it will be appreciated that where the implanted tissue consists of a Descemet membrane with the endothelial cells on one side and a thin layer of stroma on the other side, the implanted tissue is very fragile. When the cornea is processed preoperatively and later during surgical implantation in the recipient eye, endothelial cell damage may be massive, and it has been estimated that on average some 30%-40% of the cells die in the first year. This is the main cause of DSEK transplant failure.

Handling Descemet's membrane is required on two occasions. Firstly when the tissue is obtained from the donor cornea and secondly when the donor tissue is manipulated into the required position on the recipient's cornea. During both removal from the cadaver and positioning in the patient's eye, Descemet's membrane requires manipulation and positioning, typically with surgical blades, hooks and the like. These manipulations may cause damage to some or all of the endothelial cells, resulting in immediate post-operative reduction in cell number with an accumulating cell number decrease over the first year due to the death of partially damaged cells. This diminishes the likelihood of a long term successful surgical outcome.

Eye banks have been providing full thickness corneas for surgical transplantation for many years. However, with the trend towards replacement of a thin membrane only, by Descemet's stripping automated endothelial keratoplasty, (DSAEK) and to minimize the damage thereto, the donor membrane has been removed from the donor eye with the recipient patient in theatre, and the donor membrane is then immediately inserted into the patient's eye behind the cornea.

Since about 2006, eye banks have developed methodologies for precutting the center of the donor corneal tissue at the eye bank for subsequent use in surgery. For most corneal surgeons, the availability of such precut corneal tissue saves time and money, and reduces the stress of performing the donor corneal dissection in the operating room.

In surgery, a circumferential incision is made in the side of the patient's cornea. A tool is used to cut through Descemet's membrane and to detach it by upwards scraping a section that may be marked by ink on the outside surface of the cornea. The detached section is then removed through the incision. The replacement membrane from the donor is trephined out of the precut area of the donor cornea and the round thin graft is inserted through the incision in the patient's cornea and it is then manipulated into position and floated up into the scraped area by releasing an air bubble under the replacement membrane. This bubble is subsequently absorbed into the eye fluid and disappears.

Successful endothelial implantation procedures provide excellent visual outcomes due to the minimal change in corneal surface topography or refraction. They can successfully treat corneal dysfunction associated with Fuchs' endothelial dystrophy, bullous keratopathy, iridocorneal endothelial syndrome or a failed penetrating graft.

To minimize the damage to the corneal optical quality, the corneal incision is preferably as short as possible. Consequently, the diseased descemet's membrane must be folded to remove it through the short incision. The replacement Descemet's membrane must also be folded to introduce it through the incision. It will be appreciated however, that the manipulation of the donor Descemet's membrane into the patient's eye via a short incision, that is typically about 6 mm on average, with minimal damage to the endothelial cells, is a highly skilled task, requiring highly skilled eye surgeons, making the surgical procedure expensive.

In an earlier application having one common co-inventor, Israel Patent Application IL 222183, filed on 27 Sep. 2012, and then as PCT application number PCT/IL2013/050773, a dedicated apparatus and associated method for sectioning the Descemet's membrane, storing it and for manipulating it for insertion into the eye was described. The device described included a foldable base ring and cover ring that lock together with pins. It also featured a handle that extended across the diameter of the rings, under the membrane, along where the membrane was designed to fold. This promising technique has several disadvantages. Aligning the pins and holes of the two rings has been found to be rather fiddly when working manually. The handle extending across the ring has been found to risk contacting the Descemet membrane to be transplanted and to risk damaging it.

Aspects of the present invention address these issues.

SUMMARY

A first aspect is directed to a tool for endothelial implantation comprising a frame having legs for engaging a stem, such that the frame is insertable between a stroma and a Descemet's membrane, the frame being coated with a biological adhesive for adhering to a perimeter of a section of the Descemet's membrane to adhere the section of the Descemet's membrane to the frame for surgical separation of the section by cutting therearound, wherein said frame further comprises a heating element around its inner perimeter.

Typically, the entire frame serves as a heating element.

Optionally, embodiments further comprise a silicone ring configured to fit over and around the frame to secure the Descemet's membrane to the frame and to insulate the frame, preventing heat loss and electrical current short-circuiting.

In some embodiments, the frame is an open circular flat ring having a pair of legs for insertion into a stem, and the silicone ring is torroidal.

In some embodiments, the frame is coupled by the stem to a lid and the lid is sealingly attachable to a container of solution such that a specimen of Descemet's membrane attached to the frame is sealingly preservable in the solution for a time period.

In some embodiments, the stem comprises two electrical connection sockets for engaging the legs of the flat ring, said sockets being couplable to a power supply via a switch to couple the heating element to the power supply such that activation of the switch provides a current spike to the heating element for burning the perimeter of membrane to release the Descemet's membrane from the frame.

In some embodiments, the tool further comprises a retractable inserter wherein the ring is insertable into the eye via the inserter which applies a bending force to curl up the frame.

In some embodiments, the tool further comprises a switch for applying a current to the heating element to detach the (donor) Descemet's membrane from the frame.

In some embodiments, the tool further comprises an injector wherein the inserter is configurable to engage the injector, and a fluid bubble is injectable from the injector into the recipient's eye.

In some embodiments, the injector and the inserter are an integral unit.

In some embodiments, the injector comprises a syringe.

In some embodiments, the fluid is selected from the group comprising air and water.

A second aspect is directed to a method of obtaining a Descemet's membrane comprising the steps of:

Providing a tool for endothelial implantation comprising a frame having legs for engaging a stem, such that said frame is insertable between a stroma and a Descemet's membrane of a donor eye, the frame being coated with a biological adhesive for adhering to a perimeter of a section of Descemet's membrane to adhere the section of the Descemet's membrane to the frame for surgical separation of the section by cutting therearound, wherein the frame further comprises a heating element around in an inner perimeter thereof;

Obtaining a section of Descemet's membrane by separating a Descemet's membrane from a stroma of a donor eye by injecting fluid therebetween;

inserting the frame under the Descemet's membrane and adhering the Descemet's membrane to the frame using the biological adhesive, and cutting around the frame to separate the Descemet's membrane from the donor eye.

The method preferably further comprises tensioning a silicone ring over perimeter of the base ring and the Descemet's membrane adhered thereto. In some embodiments, the method further comprises immersing the frame and Descemet's membrane in a storage solution to preserve the Descemet's membrane. A further aspect is directed to a method of transplanting a donor Descemet's membrane into an eye of a recipient comprising the steps of:

Making an incision and removing a damaged Descemet's membrane from a patient via the incision;

ProvidingObtaining a descemet's membrane on a flexible framework using the method of claim 9;

Coupling each leg of the stem to electrical connection sockets, said sockets being coupled to a power supply via a switch to couple the heat element of the frame to the power supply;

Inserting the frame into a wide end of a conical inserter for applying a bending force to double over said frame;

Inserting a narrow end of the inserter through an incision into the eye;

forwarding the frame through the narrow end of the inserter into the eye;

while inside the anterior chamber of the eye, adjusting the frame with the attached tissue to the preferred location on the recipient's cornea;

Bubbling a gas into the anterior chamber under the donor attached tissue so that the air bubble causes the attached tissue to contact the recipient's cornea.

Applying a current to the heating element to detach the donor membrane from the frame around its perimeter;

allowing the membrane to float up into position;

Retracting the frame into the inserter;

Removing the inserter from the eye, and

Suturing the incision.

BRIEF DESCRIPTION OF FIGURES

For a better understanding of the invention and to show how it may be carried into effect, reference will now be made, purely by way of example, to the accompanying Figures, wherewith it is stressed that the particulars shown are by way of example and for purposes of illustrative discussion of the preferred embodiments of the present invention only, and are presented in the cause of providing what is believed to be the most useful and readily understood description of the principles and conceptual aspects of the invention.

DESCRIPTION OF PREFERRED EMBODIMENT

Figure 1:
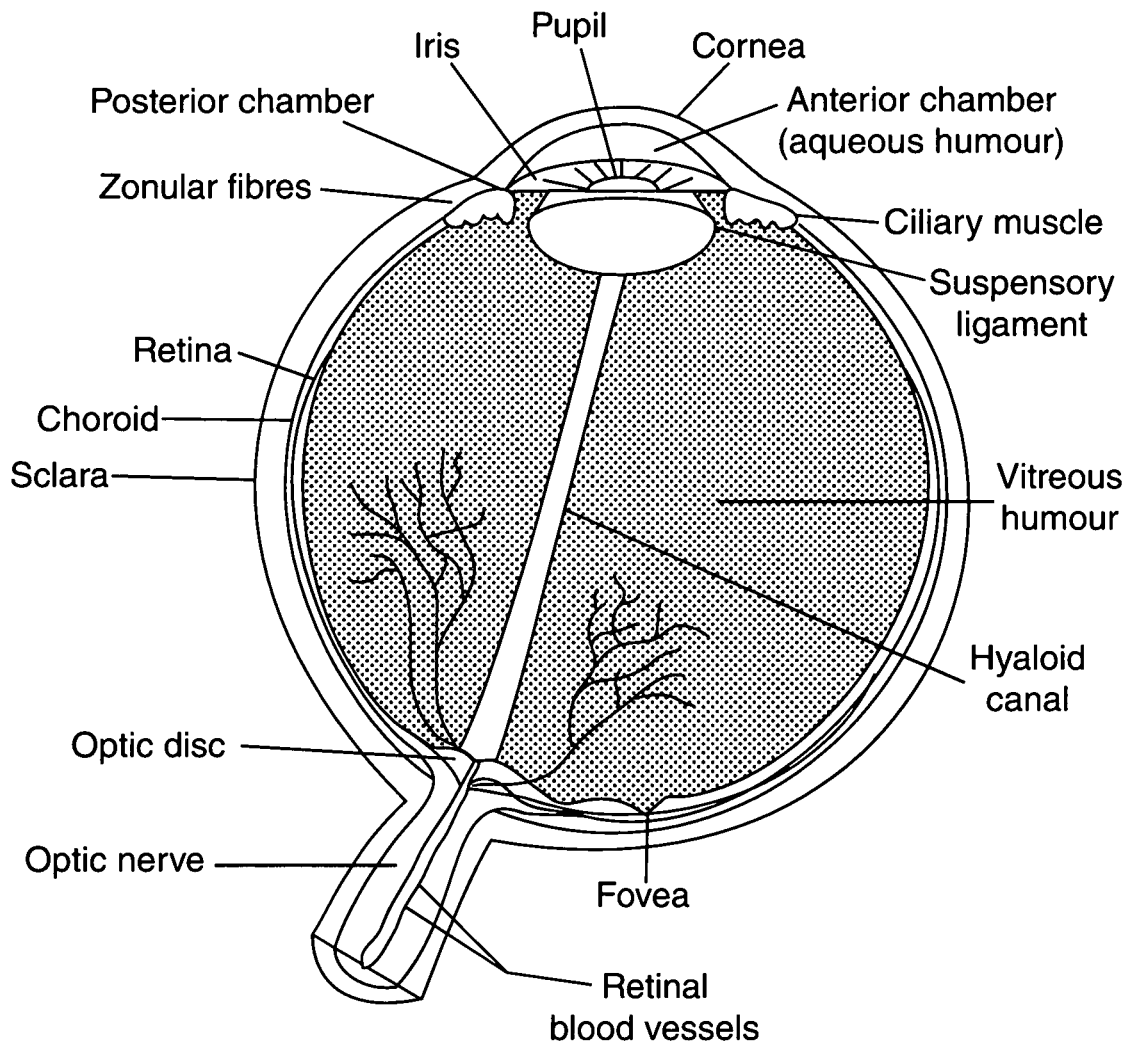
FIG. 1 is a schematic cross-sectional view of a human eye with the cornea facing upwards, in the position during surgery (prior art)

FIG. 1 is a schematic illustration of an eyeball showing the iris, pupil, cornea, lens, vitreous humour, optical nerve and other elements.

Figure 2:
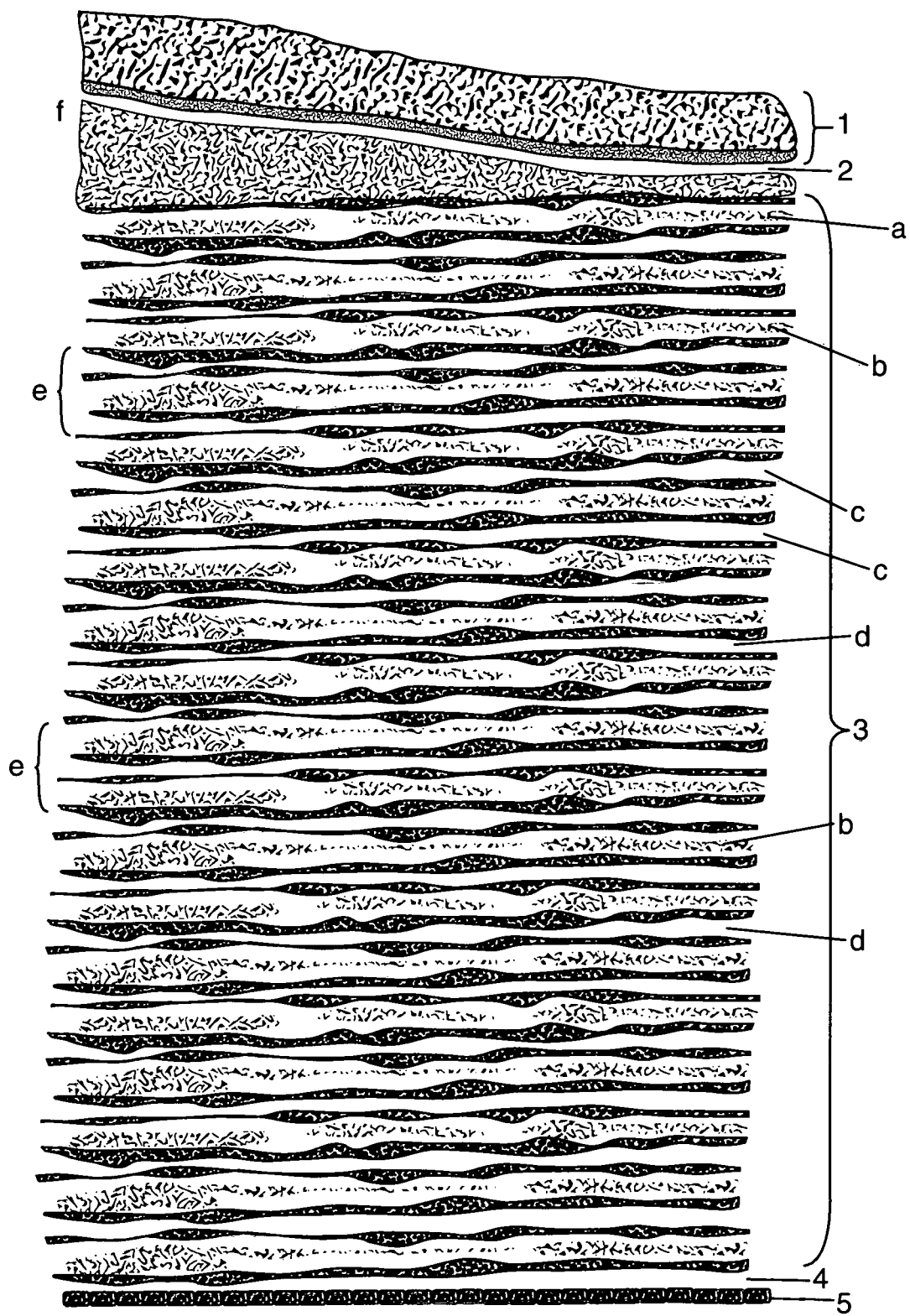
FIG. 2 is a vertical section of human cornea (taken from Gray's Anatomy) from near the margin (magnified) and showing the various layers of the cornea.

FIG. 2 is a vertical section of the human cornea from near the margin (magnified) and showing the 1. Epithelium, 2. Anterior elastic lamina, 3. substantia propria, 4. Posterior elastic lamina (Descemet's membrane), 5. Endothelium of the anterior chamber, a. Oblique fibers in the anterior layer of the substantia propria, b. Lamellae the fibers of which are cut across, producing a dotted appearance, c. Corneal corpuscles appearing fusiform in section, d. Lamellae the fibers of which are cut longitudinally, e. Transition to the sclera, with more distinct fibrillation, and surmounted by a thicker epithelium, and f. Small blood vessels cut across near the margin of the cornea.

Embodiments of the present invention are directed to improved devices and techniques for endothelial implantation, by techniques such as DSAEK—Descemet's Stripping Automated Endothelial Keratoplasty, DESK and DEMK, for example.

The devices and techniques are directed to removing the Descemet's membrane from the donor eye, storing it until required, and inserting it and positioning it in a patient's eye, whilst minimize damage to the membrane.

The devices and techniques of embodiments of the invention minimize the handling of a donor Descemet's membrane to maintain a high number of viable endothelial cells during preparation and storage. They facilitate keeping a Donor Descemet's membrane stored in a state that keeps it ready for implantation. The devices and techniques eliminate the need for direct contact with the implanted tissue during the surgical implantation phase.

It is noted that advantageously, the removal of a donor Descemet's membrane from a donor cadaver eye may be performed in advance, and does not need to be performed whilst the recipient is in surgery.

With reference to FIGS. 3*a-g*, a first technique for removing a Descemet's membrane from a donor eye is shown. The first technique uses direct mechanical separation of Descemet's membrane from the corneal stroma by pressurizing a fluid which may be air, a liquid such as water, a viscoelastic fluid or a combination of these elements via a fine cannula. The fine cannula is provided with a blunt tip to avoid puncturing Descemet's membrane during the procedure. The pressurized fluid cleaves the Descemet's membrane from the stroma.

Figure 3A:
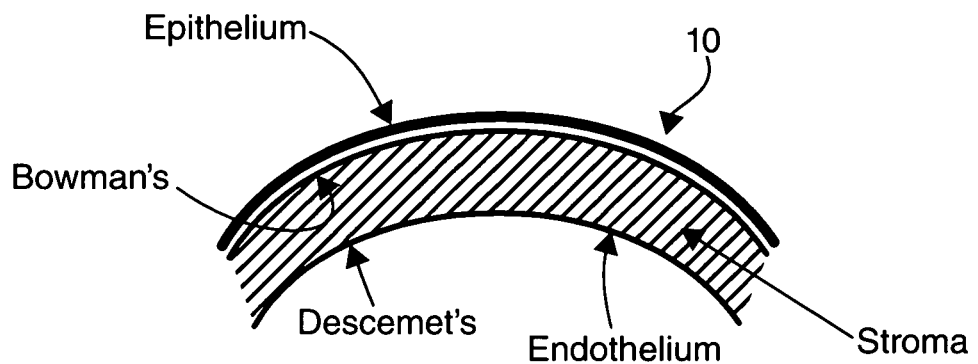
FIG. 3a is a simplified schematic view of a section of the cornea, eye facing upwards, as in a cadaver lying face upwards.
Figure 3B:
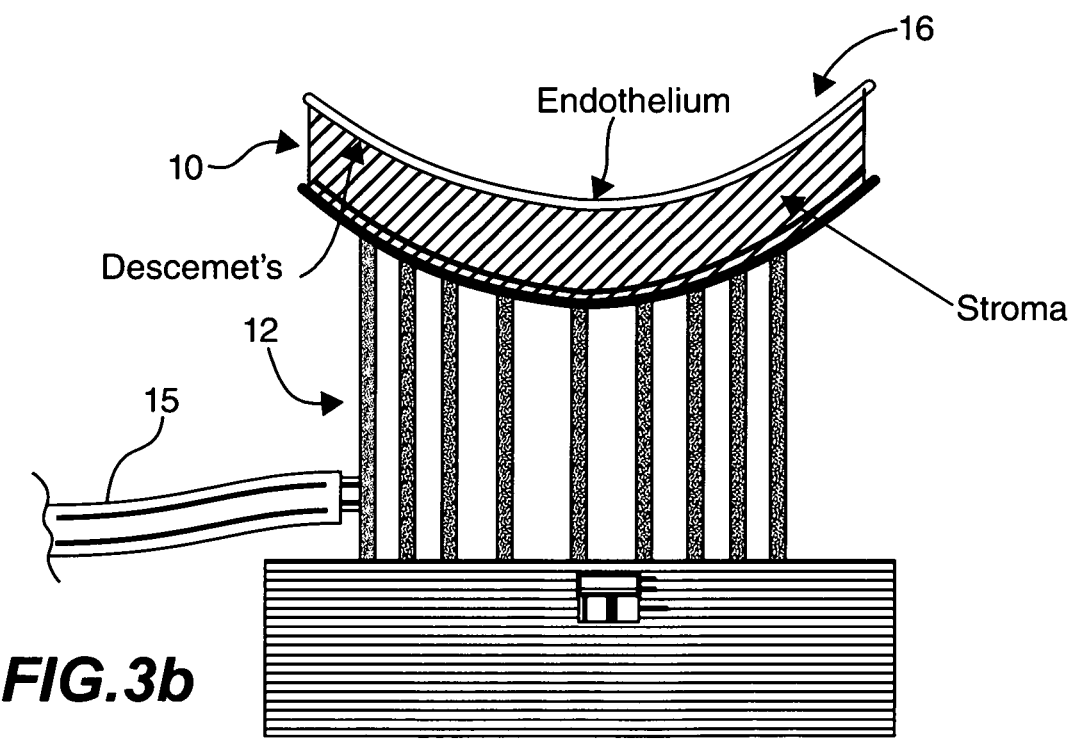
FIG. 3b is a schematic cross section showing the section of the cornea inverted and placed on a vacuum holder.

FIG. 3*a* shows the cornea of 10 of an eyeball facing upwards, such as in a cadaver positioned on its back. With reference to FIG. 3*b*, a section of a donor cornea 10 inverted and positioned on a stand 12 is shown. The cornea 10 is positioned with the Descemet's membrane 16 facing upwards. A pipe 15 connected to a vacuum pump may be used to provide vacuum suction to hold the donor cornea 10 to the stand 12.

Figure 3C:
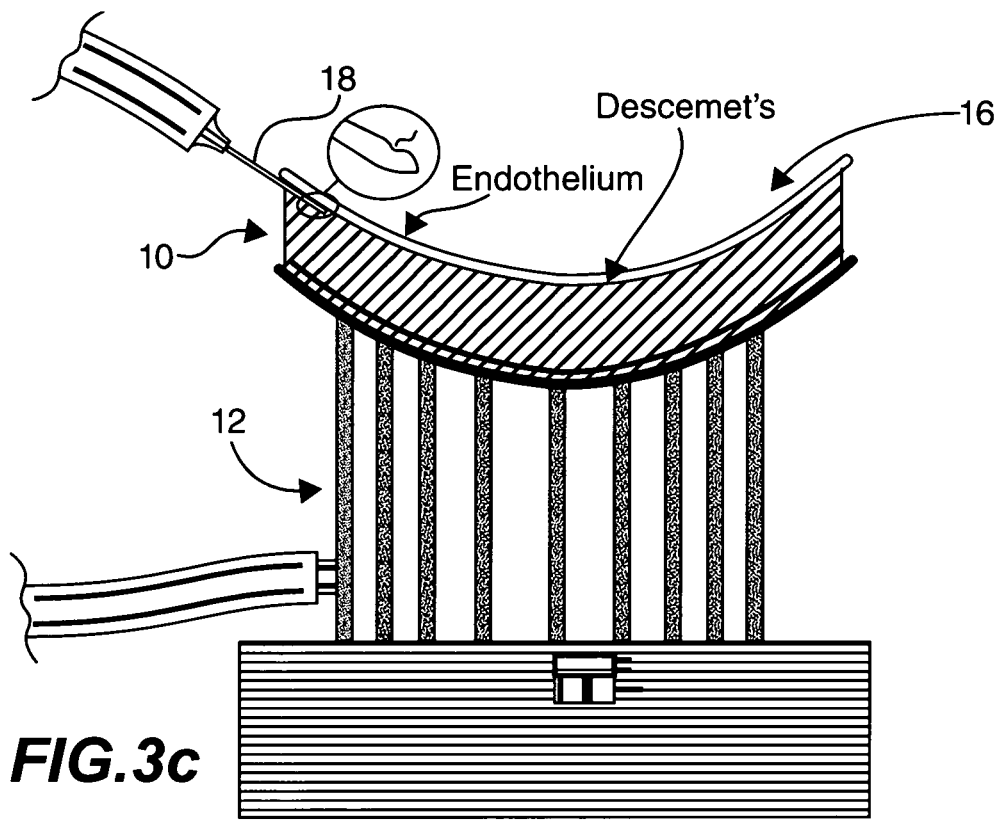
FIG. 3c is a schematic cross section showing how a blunt needle probe may be inserted into the section of the cornea under the Descemet's membrane.

Referring to FIG. 3*c*, a cannula 18 with a blunt tip may be inserted into the section of the cornea 10 and positioned such that the blunt tip and outlet of the cannula 18 are within the cornea 10, under the Descemet's membrane 16.

Figure 3D:
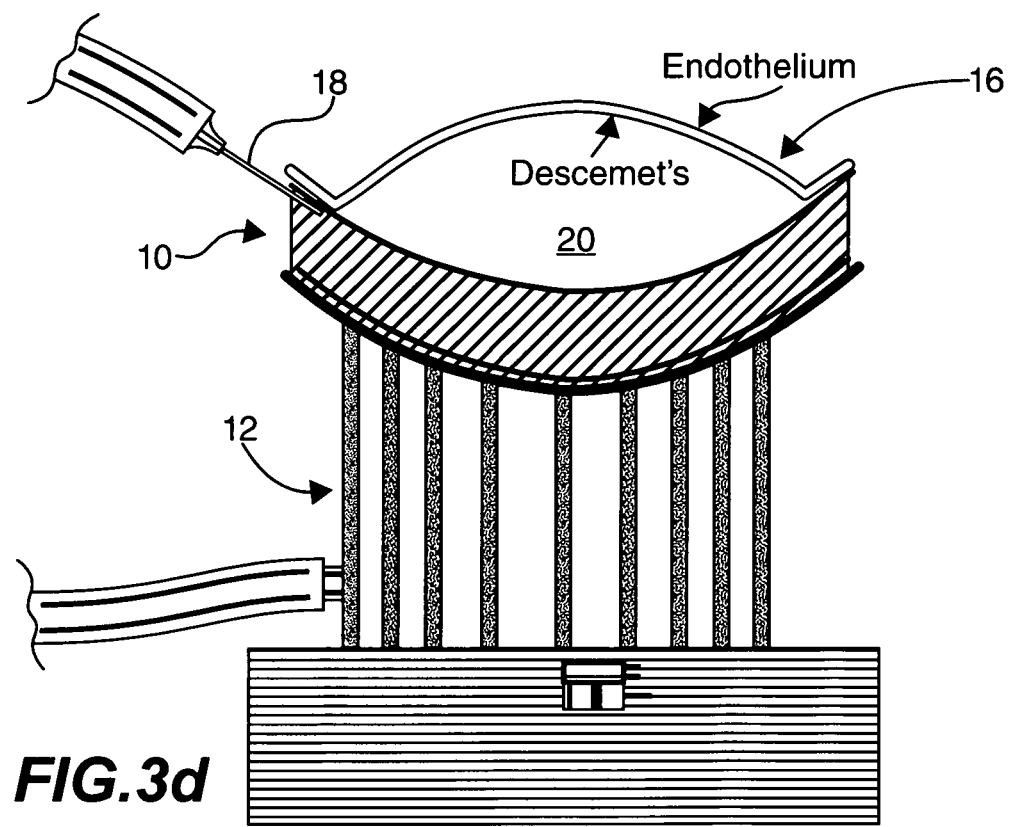
FIG. 3d is a schematic cross section showing how a cavity may be formed under the Descemet's membrane by pumping fluid via the blunt probe, under the Descemet's membrane, thereby detaching the Descemet's membrane from the stroma.

With reference to FIG. 3*d*, air or a liquid such as water or an ophthalmic solution is injected through the cannula 18 into the cornea 10, producing a cavity 20 at the end of the cannula 18 thereby tearing the Descemet's membrane 16 away from the stroma of the cornea 10.

Figure 3E:
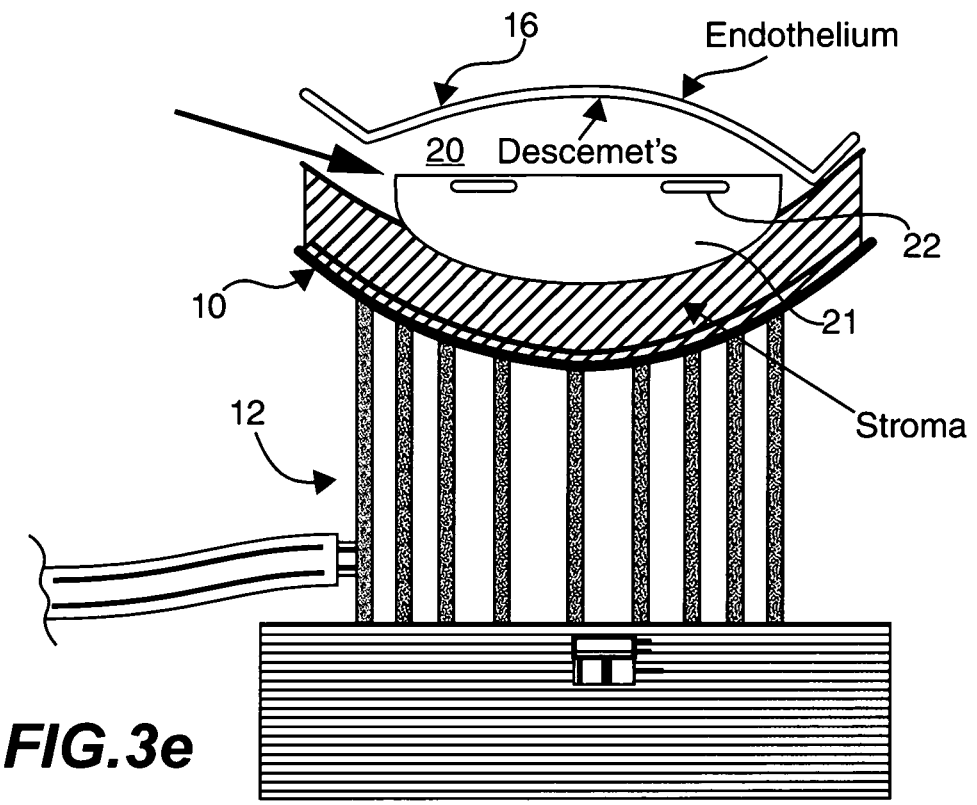
FIG. 3e is a schematic cross section showing how a frame of an embodiment may be positioned on a base and inserted into the cavity.

With reference to FIG. 3*e*, a frame 22 on a base 21 may be inserted into the cavity 20 created by the injected fluid, and positioned between the Descemet's membrane 16 and the rest of the cornea 10. The base 21 is typically a section of a sphere having appropriate curvature to the stroma and a flat upper surface provided with a socket for the frame 22.

Figure 3F:
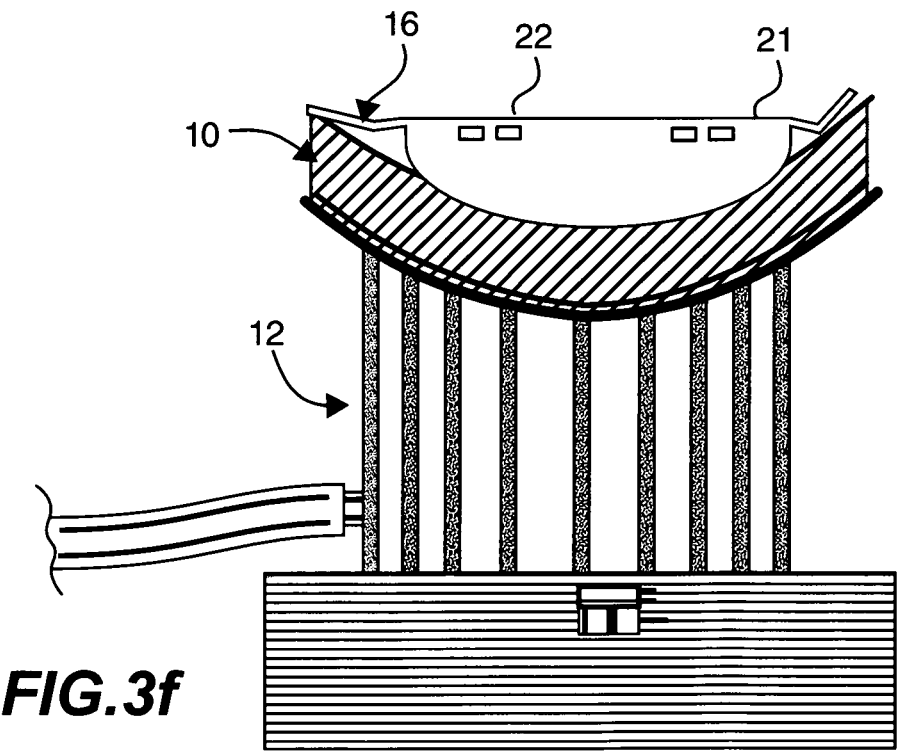
FIG. 3f is a schematic cross section showing how Descemet's membrane may be stretched over the frame and adhered to same by extracting the fluid.

As shown in FIG. 3*f*, by removing the fluid from the cavity 20, the Descemet's membrane 16 may be stretched taut over the base 21 and frame 22.

Figure 3G:
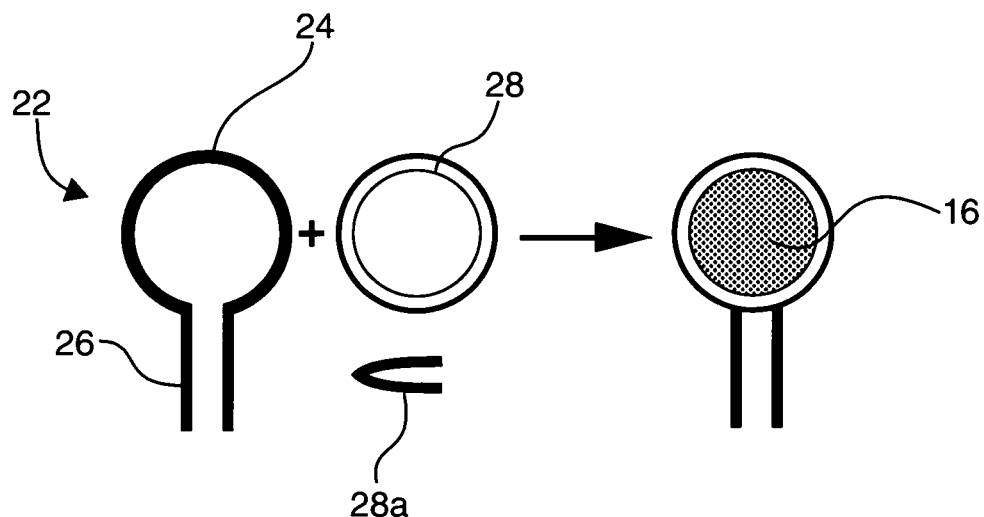
FIG. 3g illustrates a frame with legs, where the frame serves to support the Descemet's membrane and the legs serve as electrical and mechanical contacts between the frame and the body of the tool, also shown, is an elastomeric cover ring may stretched around the frame to secure the Descemet's membrane thereto.

With reference to FIG. 3*g*, in one embodiment, the frame 22 is an open flat ring 24 having two parallel legs 26. The open ring 24 is coated with a biological adhesive and the specimen of Descemet's membrane 16 is attached to the frame 22 by the adhesive.

Once a disk of Descemet's membrane 16 is adhered to the frame 22 it may be detached from the surrounding tissue of the cornea 14, with a scalpel, a laser, a cutting wire or with a circular cutter, for example. In this manner, a disk shaped piece of Descemet's membrane 16 may be removed from a donor eye 10 by contacting the perimeter of the specimen to a frame 22, without touching either surfaces of the membrane 16 within the frame 22, thereby minimizing damages to the epithelial layer.

An elastomeric ring 28 may be provided that fits around the flat ring 24 of the frame 22, and over the Descemet's membrane 16, somewhat analogous to a car tire fitting around a wheel. A cross section 28*a* through the elastomeric ring 28 is show, giving its general shape.

The elastomeric ring 28 may be fabricated from silicone, for example. The elastomeric ring 28 serves to keep the Descemet's membrane in position on the frame 22 during storage in storage solution, and enables usage of an adhesive that might dissolve into the storage solution. The elastomeric ring 28 provides thermal and electrical insulation to the part of the frame 22 covered, and when a current is applied to the frame 22, causes the heat and electrical flow to exit the frame 22 via its inner diameter only, causing a Desicmet's membrane mounted thereon, to burn through and detach from the frame 22 around its inner perimeter.

Figure 3H:
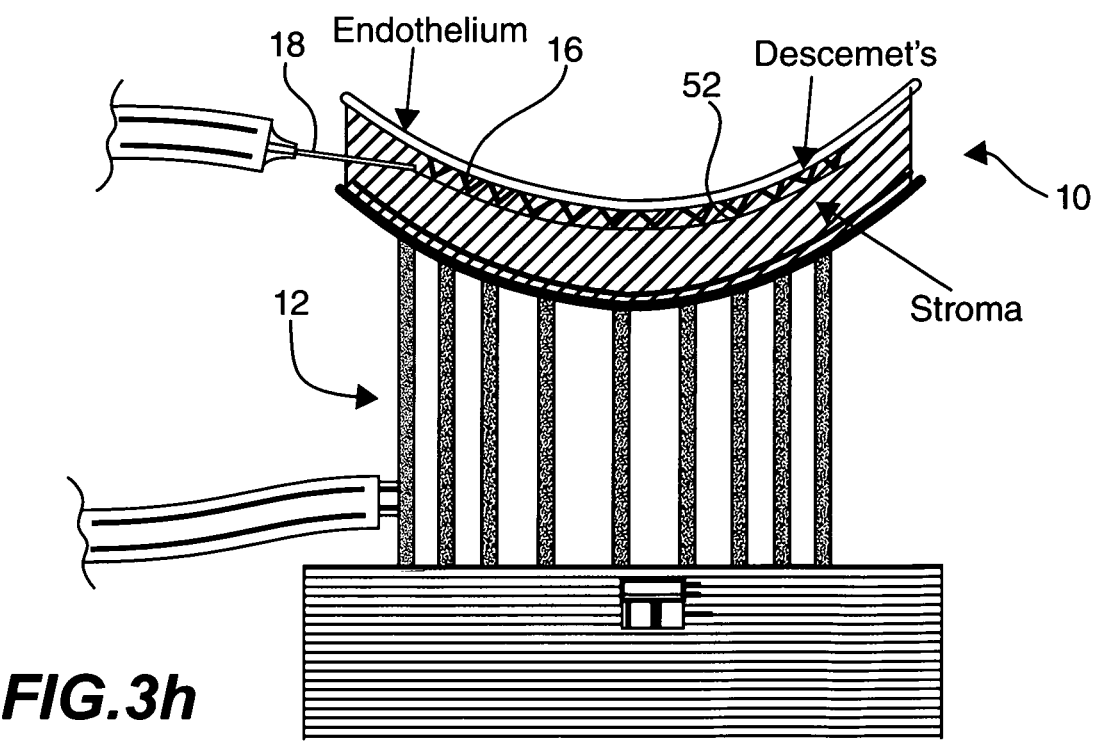
FIG. 3h shows an alternative technique for preparing a donor cornea, that uses an advanced high frequency laser to cut an accurate cleavage in the donor's cornea before removal of the cornea from the eyeball.

As illustrated in FIG. 3*h*, a second technique for removing a Decimet's membrane from a donor eye uses an advanced high frequency laser to cut an accurate cleavage 52 in the donor's cornea 10 while the whole eyeball is supported by a holder prior to removal of the cornea from the eyeball. This type of procedure is currently being used to prepare the flap cleavage during refractive surgery, for example.

Once the cleavage 52 is cut by the laser at a precise distance from the descemet membrane 16 and into the stroma, the cornea 10 including the typical scleral ring is removed from the donor eye and positioned on a vacuum stand 12 with the endothelial cells upwards. The laser induced cleavage 52 is then filled with air or fluid or viscoelastic using the blunt tip cannula 18 and the entry site is widened to enable the insertion of the ring holder into the cleavage 52 and the process continues as described for the first separation method. This second technique is an important variant since it enables implants with a designated thickness to be prepared. This may be useful since some corneal pathology extends to the deeper stroma and in such cases, replacement of only the endothelial cells may be insufficient to provide the needed optical clarity. Measuring the location of such lesions in the deep sclera enables the graft thickness to be accurately prepared by this laser technique. The corresponding cleavage in the recipient eye may also be prepared using the same laser technology, resulting in the implanted tissue exactly matching the diameter and thickness of the material it replaces.

Figure 4A:
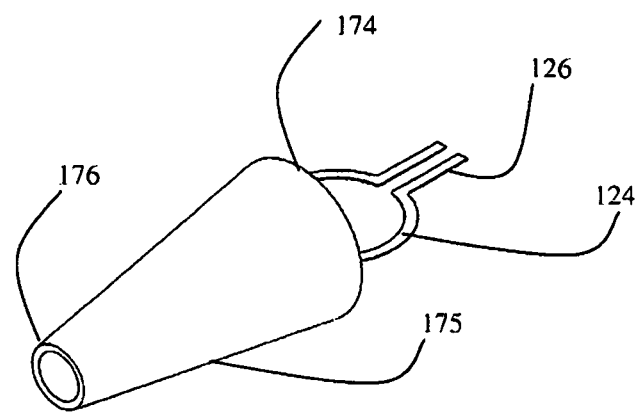
FIG. 4a is a schematic illustration of a frame on a stem, being positioned into a conical inserter.

Referring now to FIG. 4*a*, an open frame 124 is shown being inserted into the wide end of an injector head 175 having a truncated conical shape. Legs 126 of the frame 122 may be coupled to a stem 140 provided with sockets 136, 137 for engaging the legs 126 of the frame 124. Sockets 136, 137 provide mechanical support to the frame 126, and also enable electrical contract thereto.

The injector head 175 has a truncated conical shape, and is typically filled with a viscoelastic, biocompatible fluid that reduces friction on the frame 124 and provides a counter pressure when inserted through an incision in the membrane of the eye.

Figure 4B:
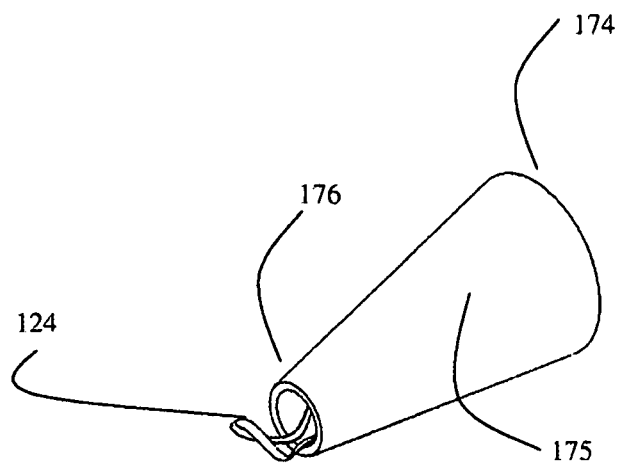
FIG. 4b is a schematic illustration of the frame on a stem being forwarded through the conical inserter, showing how it exits the narrow front end of the inserter in a curled up and doubled over manner.

As shown in FIG. 4b, as the frame 124 is pushed through the inserter head 175, the gradually tapering surface of the inserter head 175 causes the frame 124 to curl up and double over. The diameter of the wide end 174 of the inserter head 174 may be about 12 mm to accept a large disc of Descemet's membrane. The narrow end 176 of the inserter head 175 may be a mere 4 mm across.

Figure 5:
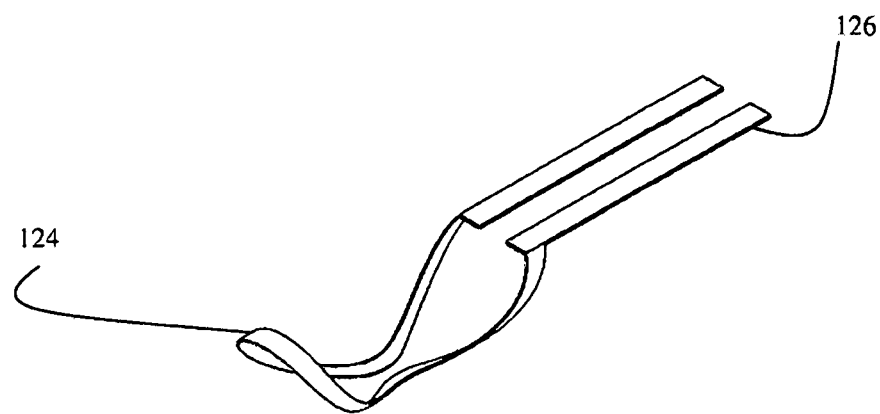
FIG. 5 shows the curled up and doubled over frame in its curled up configuration caused by its passing through the conical inserter, to enable insertion through a small incision in the cornea.
Figure 6:
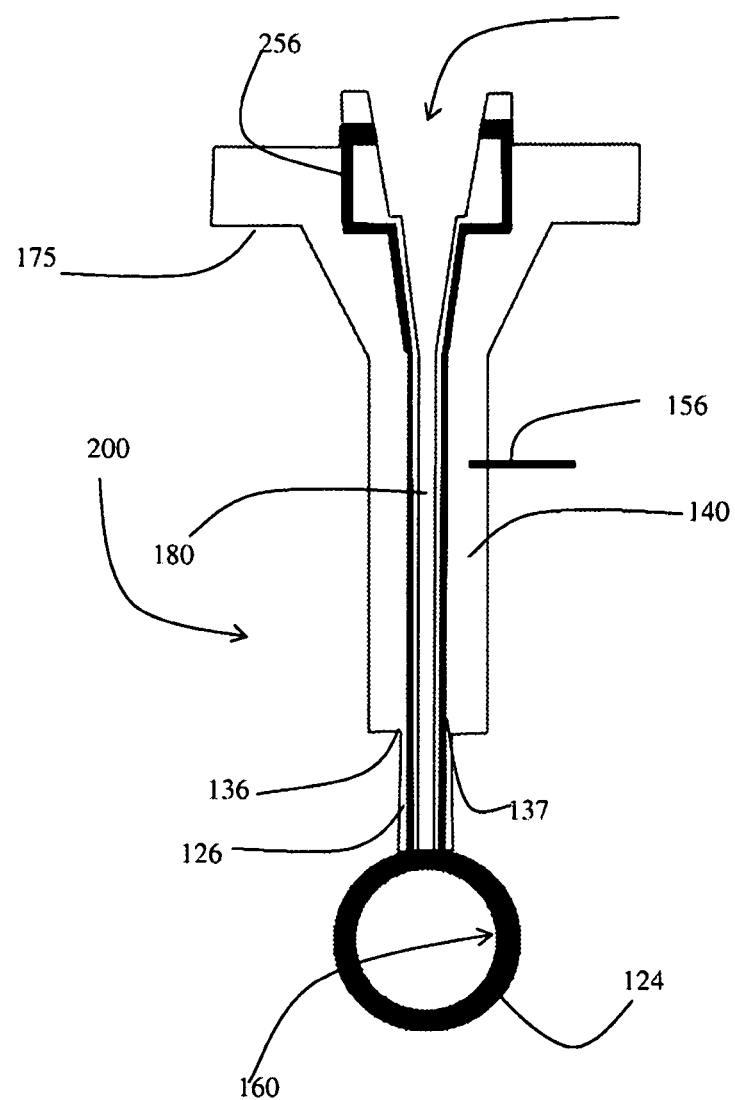
FIG. 6 is a schematic illustration of a tissue holding assembly that may be inserted into a jar of preservation fluid or coupled to a syringe.

With further reference to FIG. 5, the curled up frame 124 is compact and has outer dimensions of about 4 mm, and can be pushed through the narrow end 176 of the inserter head 175.

The narrow end 176 of the inserter head 175 may be inserted into an incision made in the sclerotic membrane of the eye that may be 5 or 6 mm long. The frame 124 may be pushed through the inserter head 175 and once one half of the frame 124 exits the narrow end 176 of inserter 175, the frame 124 starts to expand and regain its non-compressed, circular shape.

With reference to FIG. 5, the frame 124 is provided on a stem 140. The tissue holding assembly 142 comprising the frame 122 and silicon holding ring 124 on the stem 140 with a trapped specimen 116 of Descemet's membrane 16 harvested from a donor eye may be lowered into a jar filled with a standard clinically approved preserving solution that may be used for corneal preservation and the lid 175 closed to the jar, to seal it, protecting the tissue specimen 116 from contamination and keeping it moist in an appropriate preservation solution. In this manner, a disk shaped specimen 116 of Descemet's membrane 16 may be removed from a donor eye 10 and stored until needed.

The above described tissue holding assembly 142 is a convenient way of obtaining and storing a quality section of Descemet's membrane 116 for subsequent implantation.

The frame 124 is preferably a few hundred microns thick, perhaps 0.5 mm thick, and defines an inner space of the clinically favored implanted tissue size, which is currently between about 7.0 mm and 8.0 mm. Typically, the frame 124 is circular and the space it defines is a disk shape. Other shapes, such as ellipses and oblongs are, however possible.

The outside diameter of the frame 124 must be sufficient to maintain its round shape and to be semi-rigid. Preferably, the outer diameter of the frame is about 9.0 mm to 10.0 mm. Frame 124 may be fabricated from a plastic, a metal or an alloy that is able to be bent and flexed. It may be provided with thinner sections or other adaptations that facilitate it folding along an access between the arms.

Arms 126 of the frame 124 are coated with an insulating material, and the frame 124 is covered with the elastomeric ring 28 which also provides thermal and electrical insulation. Preferably, the stem 140 further comprises a cannula 180 that is couplable to a gas supply. The cannula 180 runs along the stem 140 of the tissue holding assembly 142, allowing fluid, typically air to be injected from a syringe, for example, to release a gas bubble from the syringe or other gas supply, under the Descemet's membrane 116 to float it up and away from the frame 124.

The stem 140 is a rigid structure that is typically about 30 mm to 50 mm long and comprises two elements provided with sockets 136, 137 for receiving and electrically coupling the legs 126 of the frame 124. under the A slider 156 or other type of activator, may be affixed to the tissue holding assembly 142, or to the inserter head 175 (FIG. 7) and operated by the thumb or by a finger to insert or extract the tissue holding assembly 142 through the inserter head 175.

Preferably, the overall outer dimensions of the stem 140 are between 0.5 mm to 1.0 mm in outer diameter and it preferably has an oval cross section.

It will be noted that folding a detached section of a patient Descimet's membrane for removal via a circumferential incision in the cornea and insertion of a donor membrane 16 is known. However, in the prior art the membrane is folded and unfolded using hooks and blades and consequently, a number of the epithelial cells become damaged in the process.

In contradistinction, an embodiment of the present invention is directed to providing a toolset that includes the above tissue holding assembly, but is designed to implant a section of a donor's Descimet's membrane 116 into a patient's eyeball with minimum handing of the section 116, thereby minimizing the risk of damage thereto.

It will be appreciated that for insertion into a patient's eye, an incision is required in the cornea. By enabling the frame 124 to be folded, the frame 124, and silicone ring 128 where provided, and Descimet's membrane 116 adhered to the frame may be inserted through a small incision into a patient's eye.

Figure 7:
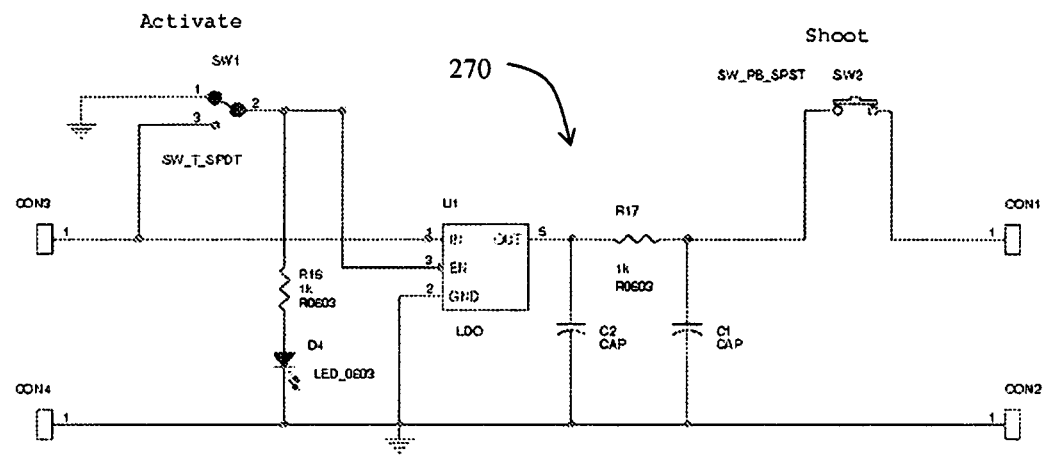
FIG. 7 is a circuit diagram of an electronic circuit for applying a pulse to the heating element to burn through and detach the membrane.

By way of example, FIG. 7 shows a circuit diagram of a circuit that may be used to provide an electric signal to the frame for providing a controlled pulse of current to the heating element to burn through and detach the donor Descemet's membrane 116 from the frame 124.

Figure 8:
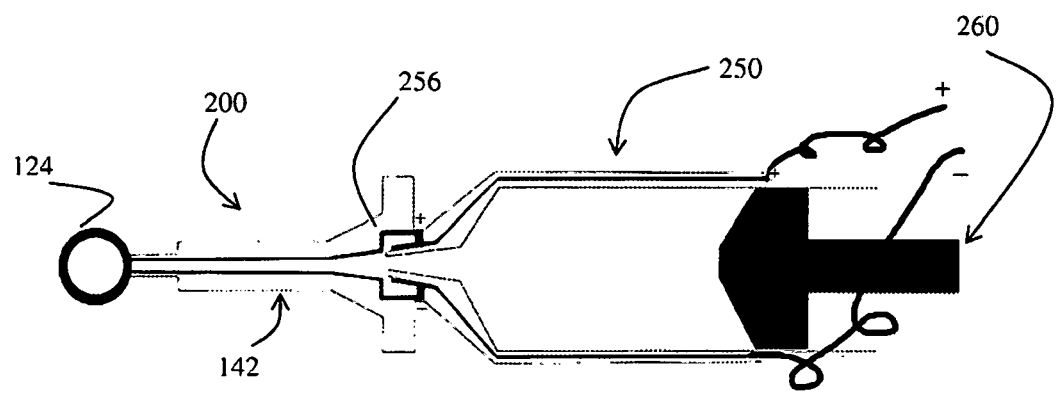
FIG. 8 is a section through the tissue holding assembly of FIG. 7 connected to an injector comprising a micro-syringe for providing an air bubble under the Descemet's membrane.

With reference to FIG. 8, the tissue holding assembly 142 is designed for coupling to a fluid injector 250 or syringe. The tissue holding assembly 142 and injector 250 may be provided as a single component of as separate components, which may be easier to sterilize and more convenient. By bending the frame 124, it may be inserted through a short insertion made in the cornea, during surgery.

For sterilization purposes it may be preferable for the tissue holding assembly 142 and the injector 250 to be separate components that may be joined together, preferred by an interlock mechanism, prior to implantation. Alternatively, the tissue holding assembly 142 and the injector 250 may alternatively be provided as a single unitary tool.

As shown in FIG. 7 in more detail, a capacitor circuit 270 may be provided. A short high current pulse is passed around the frame 124 or through the heating element 160. This generates heat and burns through the edge of the donor membrane specimen 116 adhered to the frame 122, thereby releasing the donor membrane specimen 116. The elastomeric ring provides thermal and electrical insulation to the flat surfaces and outer surface of the frame 124 and ensures that the heat flux is through the inner surface only.

Wires coupled to the frame 124 may pass along the stem 140 and be connected to a power source within the injector 250, or to a separate power source coupled therewith.

Torroidal heating element 160 may be fabricated from a high resistance biomaterial such as a Nickel Chromium alloy. The torroidal heating element 160 is electrically coupled to electrical conducting wires of lower resistance, say copper, that extend along the stem 140. In some embodiments, the stem 140 itself is fabricated from a metal. In such embodiments, the electrical wires are jacketed to insulate them from the stem 140.

The injector 250 may be detachably coupleable to the inserter 200 assembly, and the contact points on each component may be aligned when coupling the tissue holding assembly 142 to the injector 250.

Thus where the tissue holding assembly 142 and injector 250 are separate components, the wires through the stem 140 may be terminated with sockets 136, 137 for connectively engaging corresponding connecting elements on the injector 250. Thus coupling the injector 250 to the inserter 200 requires a mechanical coupling mechanism for attaching the injector 250 to the stem 140, and electrical contacts for providing electrical connections for allowing a current to be supplied to the heating element 160.

In a variant assembly, the connecting apparatus comprises of a two level structure. The lower level contains a holding element for the connecting element with the stem and the frame 122. This holding element may consist of a sprung bayonet clip, or may consist of a ring element locked to the inner side of the connecting element by a semi-circular movement of the holding element and a spring mechanism that pushes the holding element upwards at the end of the semi-circular movement to avoid spontaneous release. The diameter of the holding element is larger than the diameter of the joined semi flexible rings to enable smooth passage of the joined semi-flexible ring of non-conducting material in its expanded, unfolded configuration, through the connecting apparatus once the holding element is released. Preferred dimensions of the holding element are about 15 mm to 20 mm in diameter. Under the holding element, the inner part of the connecting apparatus is threaded to be screwed to the top of the container that houses the tissue. The leading end of the screw has a serrated shape to match its counter shape at the end of the screwing process therefore irreversibly lock the connecting apparatus to the container. The upper level of the connecting apparatus is connected to the lower level by a thin breakable material located just above the attachment of the holding element with the inner aspect of the connecting apparatus. This two layer arrangement facilitates maintaining the contained tissue and its holding apparatus sterile.

Referring to FIG. 8, the second element, the injector 250, may consist of a small 3 to 5 ml syringe 260 having a modified connecting end. On both sides of the tip at the connecting end there is an exposed electrical contact point adjusted to connect with the contact points of a connecting element to complete an electrical circuit with the heating element 134 that is positioned between the interlocked nonconducting rings 122, 124. Behind the connecting tip of the injector 250 a switch 256 may be positioned. The switch 256 is connected in series with the heating element 160 and may be a push button switch, for example. It is preferably visible and accessible once the Injector 250 is interlocked with the inserter 200. Depressing the switch 256 sends a pulse of electricity to the heating element 160 which burns through the perimeter of the membrane attached thereover, releasing the membrane.

The syringe 260 of the injector 200 may be filled with air or liquid which may be released via a cannula 180 through the stem 140. Fluid may be ejected from the cannula 180 by depressing the plunger 260 of syringe 250 in a typical injecting procedure. Alternatively, instead of introducing fluid via the stem 140, a syringe 250 may be coupled to a separate needle positioned behind the membrane 116.

Embodiments of the invention are thus directed to a tool for removing a section of Descemet's membrane 16 from a donor eye, and for inserting the section into a recipient patient's eye.

In one embodiment, the tool comprises: a distal end consisting of a frame with legs that engage sockets of a stem; a silicone ring for covering the frame; a mechanism for causing the frame to bend. The tool further comprises a heating element in the frame that is coupled to a power supply via the stem, such that air or water pressure released from the injector may be used to detach the Descemet's membrane from the stroma in the donor eye and the frame may be inserted under the Descemet's membrane. The frame may be coated with a bioadhesive for attaching the Descemet's membrane. A silicone ring may then be tensioned around the frame to lockingly engage the membrane to the frame. The Descemet's section may now be separated from the surrounding eye tissue, using a scalpel or other cutting tool.

Preferably, the distal end of the tool is lockingly insertable into a container of preservation fluid for sealingly storing the section of Descemet's membrane.

To insert into the patient's eye, a bending force is applied to the frame 124 that causes the frame and trapped donor descemet membrane section to bend and curl. The curled membrane may be inserted through a short incision in the cornea, as used for extraction of the diseased Descemet's membrane. Once inserted through the incision and positioned under the hole in the Descemet's membrane, the bending force may be eased and the rings assume their flat, circular shape. Application of electrical power to the ring or to a heating element which is a high resistance conductor, burns through the Descemet's membrane releasing the inner disk of Descemet's membrane. Preferably the stem further comprises a cannula. Bubbling a gas, such as air, or a liquid such as water from the injector 250 under the disk causes it to float up and join the surrounding Descemet's membrane of the patient.

The technique of floating the membrane up using air bubbles is known. The air may be inserted using a separate air pipe or needle. However, in preferred embodiments, the air pipe is integral to the tool of the invention and is a cannula that passes down the stem.

Thus a tool is described that can be used for both excising a section of Descemet's membrane from a donor eye, and for releasing the section to be floated into position in a recipient patient's eye. The Descemet membrane is manipulated by the edges of the section to be implanted and the section to be implanted is not contacted with knives, hooks and the like, and thus the tissue inserted is suffers less damage than conventional techniques.

The membrane is released by simply burning the tissue at the perimeter of the sample, which is usually circular, detaching the sample from the holder rings.

Preferably the holder with membrane is insertable into a preservation solution and may be stored for a several hours, days or even a few weeks.

Figure 9:
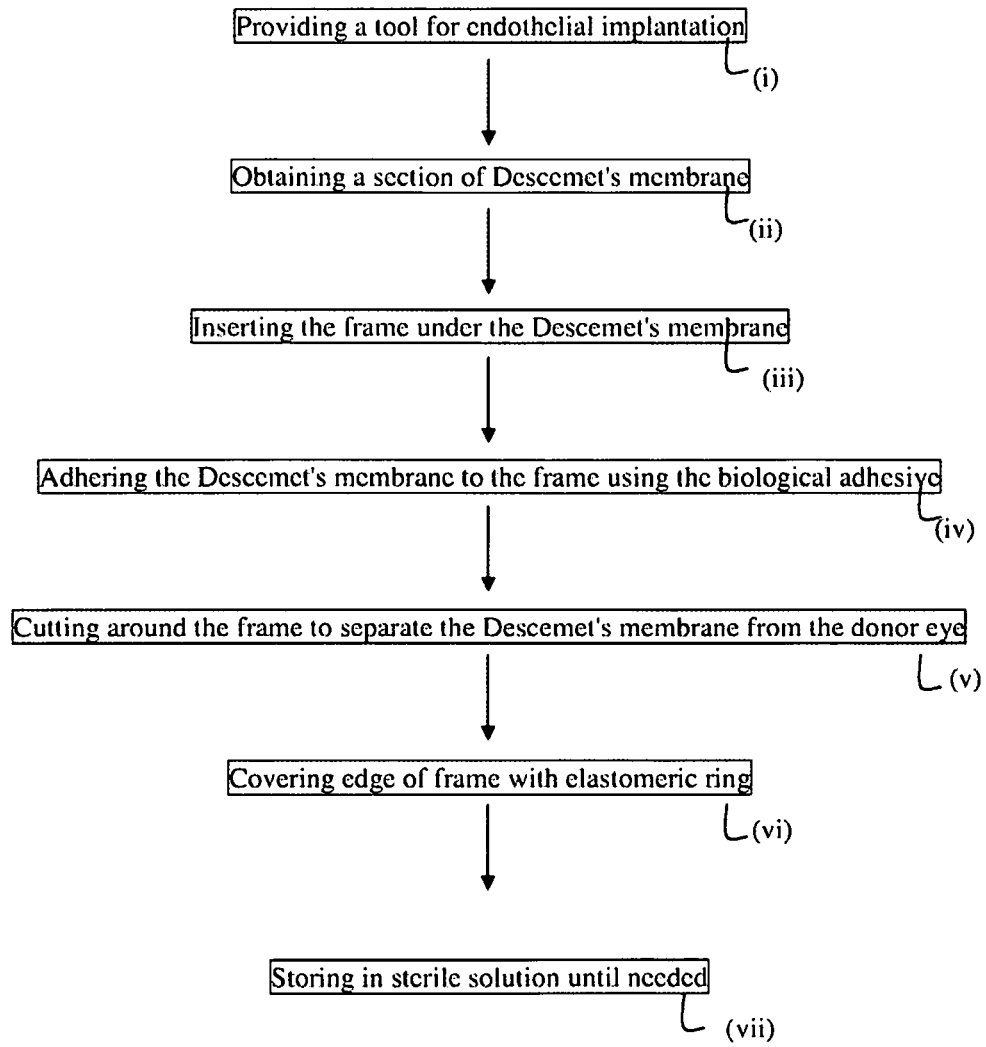
FIG. 9 is a flowchart of steps for preparing a donor Descemet's membrane for transplanting.

With reference to FIG. 9, an aspect of the invention is directed to a method of obtaining a Descemet's membrane comprising: (i) Providing a tool for endothelial implantation comprising a frame having legs for engaging a stem, such that said frame is insertable between a stroma and a Descemet's membrane of a donor eye; the frame being coated with a biological adhesive for adhering to a perimeter of a section of Descemet's membrane to adhere the section of the Descemet's membrane to the frame for surgical separation of said section by cutting therearound, wherein said frame further comprises a heating element around in an inner perimeter thereof; (ii) Obtaining a section of Descemet's membrane by separating a Descemet's membrane from a stroma of a donor eye by injecting fluid therebetween; (iii) inserting the frame under the Descemet's membrane; (iv) adhering the Descemet's membrane to the frame using the biological adhesive; (v) cutting around the frame to separate the Descemet's membrane from the donor eye; (vi) covering the frame and edge of the membrane with an elastomeric, insulating protection ring, and (vii) storing in sterile storage solution until needed.

Figure 10:
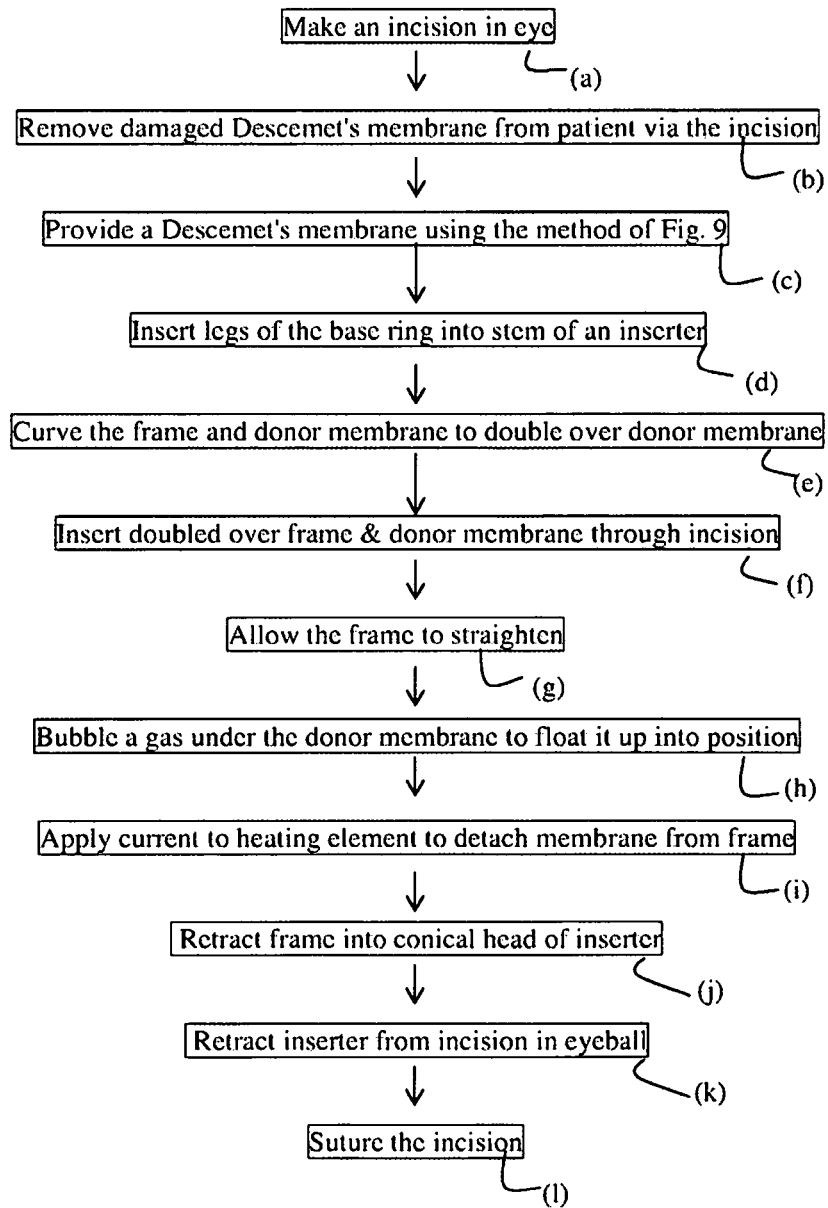
FIG. 10 is a flowchart detailing a method for performing a Descemet's membrane replacement procedure using the tool of FIG. 1.

With reference to FIG. 10, a method for replacing the Descemet's membrane consists of making an incision in the eye—step (a) and removing a damaged Descemet's membrane from a patient via the incision—step (b); Providing a Descemet's membrane from a donor, mounted on a frame as per the method described hereinabove with reference to FIG. 9, inserting the legs of the frame into a stem of an inserter—step (d). The stem may consist of two electrically connection sockets for engaging the legs of the flat ring. These sockets may be coupled to a power supply via a switch to couple the frame to the power supply. The inserter may have a truncated cone shaped end which may be inserted into an incision made in the scelatic membrane. The frame and donor membrane are curled up by pushing through the conical inserter reaching maximal curling at the narrow end of the conical inserter which is positioned inside the anterior chamber of the eye.—step (e).

The doubled over frame and donor membrane are now pushed through the narrow end of the conical inserter and through an incision into the eye—step (f). Further advancing of the frame causes it to straighten out—step (g). Bubbling a gas under the donor membrane allows it to be moved into position—step (h). By applying a current to the heating element, the donor membrane may be detached from the frame—step (i). The frame is pulled out and extracted via the conical inserter from the eye (note that it must be done via the inserter otherwise the frame might damage the cornea during the pulling out process—step (j). Then the inserter itself is retracted from the incision—step (k) and the incision may now be sutured—step (l).

Preferably, the stem further comprises a cannula that is couplable to a gas source and the method comprises coupling said inserter to an injector before inserting the conical end of the inserter into the eye, and after straightening the membrane within the eye, sliding the cannula forwards to extend under the Descemet membrane to bubble a gas from an injector under the membrane.

It will be appreciated that the present invention is capable of significant variation. Thus the scope of the present invention is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

The invention claimed is:

1. A tissue holding apparatus configured for implantation of a membrane section into a recipient's eye through an incision in said recipient's eye, the tissue holding apparatus comprising:
   a) a flexible, curved membrane support configured to bear said membrane section where said membrane section is folded over said flexible curved membrane support; and
   b) a curved elastomeric holder having a generally C-shaped cross-section, and configured to be peripherally mounted around said membrane section folded over said flexible, curved membrane support to secure said membrane section to said flexible curved membrane support, wherein said flexible, curved membrane support, said membrane section and said curved elastomeric holder together form a combined structure configured to be temporarily curled upon itself for insertion through the incision into the recipient's eye.

2. The tissue holding apparatus of claim 1, wherein said combined structure is configured to be curled as a unit by an external inserting device.

3. The tissue holding apparatus of claim 1, wherein said flexible curved elastomeric holder comprises silicone.

4. The tissue holding apparatus of claim 1, wherein said flexible curved membrane support has adhesive properties capable of holding said membrane section thereto.

5. The tissue holding apparatus of claim 1, wherein said flexible curved membrane support comprises a biological adhesive.

6. The tissue holding apparatus of claim 1, wherein said flexible curved membrane support comprises a circular shape.

7. The tissue holding apparatus of claim 1, wherein said flexible, curved elastomeric holder is a closed structure.

* * * * *